United States Patent [19]
Masterson et al.

[11] Patent Number: 5,580,580
[45] Date of Patent: Dec. 3, 1996

[54] FORMULATIONS AND THEIR USE IN THE TREATMENT OF NEUROLOGICAL DISEASES

[75] Inventors: Joseph G. Masterson, London, United Kingdom; Michael Myers, Athlone, Ireland

[73] Assignee: Elan Corporation, plc, Athlone, Ireland

[21] Appl. No.: 479,506

[22] Filed: Jun. 7, 1995

Related U.S. Application Data

[62] Division of Ser. No. 328,165, Oct. 24, 1994, abandoned, which is a division of Ser. No. 73,651, Jun. 7, 1993, Pat. No. 5,370,879, which is a continuation of Ser. No. 786,400, Nov. 1, 1991, abandoned.

[30] Foreign Application Priority Data

Nov. 2, 1990 [IE] Ireland .................................... 3952/90

[51] Int. Cl.6 ............................... A61K 9/16; A61K 9/50; A61K 9/62; A61K 9/70
[52] U.S. Cl. .................. 424/490; 424/445; 424/449; 424/451; 424/452; 424/458; 424/460; 424/462; 424/464; 424/465; 424/474; 424/475; 424/480; 424/484; 424/489; 424/494; 424/495; 424/497; 424/498; 424/499
[58] Field of Search ...................... 424/445, 449, 424/451, 452, 458, 460, 462, 464, 465, 474, 475, 480, 484, 489, 494, 495, 497, 498, 499

[56] References Cited

U.S. PATENT DOCUMENTS

| | | | |
|---|---|---|---|
| 4,386,095 | 5/1983 | Gibson et al. | 514/352 |
| 4,562,196 | 12/1985 | Horn et al. | 514/332 |
| 4,721,619 | 1/1988 | Panoz et al. | 424/459 |
| 4,894,240 | 1/1990 | Geoghegan et al. | 424/497 |
| 4,946,853 | 8/1990 | Bannon et al. | 514/343 |

FOREIGN PATENT DOCUMENTS

| | | | |
|---|---|---|---|
| 0117027 | 1/1984 | European Pat. Off. | A61M 37/00 |
| 0113562 | 7/1984 | European Pat. Off. | A61M 37/00 |
| 0156077 | 10/1985 | European Pat. Off. | |
| 0325843 | 8/1989 | European Pat. Off. | |

OTHER PUBLICATIONS

Davis et al, D. of the Rush Multiple Sclerosis Center.
Bever et al, Ann Neurol. 27(4), pp. 421–427 (Apr. 1990).
Wesseling et al, N. Eng. J. of Med, 310(15), pp. 988–989 (Apr. 1984).
"4–Amino Pyridine Tablets; A Method for the Preparation [and] in Vitro and in Vivostudies", Uges et al., Pharm. Acta Helu., 57(4) pp. 122–128, 1982, Abstract.
"4 Aminopyridine in the Treatment of Alzheimer's Disease", Davidson et al., Biol. Psychiatry 23(5), 1988 pp. 485–490.
"4 Aminopyridine Improves Clinical Signs in Multiple Sclerosis", Stefoski et al, Ann Neurol 21(1), 1987, pp. 71–77.
Barker, S. & Branford, D.; Pharm Journal Jan. 26, 1991, pp. 116–118.
Bever, C.T. Jr.: Leslie, J,; Camenga, D.L.; Panitch, H.S.; and Johnson, K.P., Ann. Neurol. 27(4), pp. 421–427 (Apr. 1990).

*Primary Examiner*—Carlos Azpuru
*Attorney, Agent, or Firm*—Marla J. Church

[57] ABSTRACT

Pharmaceutical formulations comprise a mono- or di-aminopyridine active agent for administration on a once- or twice-daily basis for use in the treatment of neurological diseases, in particular multiple sclerosis and Alzheimer's disease. The formulations, which are suitable for oral or percutaneous administration of the active agent, include the active agent in a carrier effective to permit release of the mono- or di-aminopyridine at a rate allowing controlled absorption thereof over, on the average, not less than a 12 hour period and at a rate sufficient to achieve therapeutically effective blood levels over a period of 12–24 hours following administration.

8 Claims, 1 Drawing Sheet

4-AP % RELEASE

4-AP % RELEASE

FORMULATIONS AND THEIR USE IN THE TREATMENT OF NEUROLOGICAL DISEASES

This is a divisional of application Ser. No. 08/328,165 filed on Oct. 24, 1994, now abandoned, which is a divisional of Ser. No. 08/073,651, filed on Jun. 7, 1993, now U.S. Pat. No. 5,370,879, which is a continuation of Ser. No. 07/786,400, filed Nov. 1, 1991, now abandoned.

FIELD OF THE INVENTION

This invention relates to preparations for use in the treatment of neurological diseases. More particularly, the invention relates to preparations for the controlled administration of mono- or di-aminopyridine active agents and to the use of such preparations in the treatment of neurological diseases characterised by a slowing of nerve impulse transmission, more especially multiple sclerosis and Alzheimer's disease.

BACKGROUND AND PRIOR ART

Multiple sclerosis (MS) is a degenerative and inflammatory neurological disease which affects the central nervous system, more specifically the myelin sheath. MS causes demyelination of nerve fibres resulting in short-circuiting of nerve impulses and thus a slowing or blocking of transmission along the nerve fibres, with associated disabling symptoms.

Alzheimer's disease is a major cause of dementia in the elderly. It may be described as a progressive pathological deterioration in personality, memory and intellect consistent with a generalised atrophy of corresponding brain centres. The emotional state, behaviour, cognitive function and thought processes of sufferers are all adversely affected. A minor disimprovement in memory which gradually becomes more apparent is the first indication of the onset of the disease.

The incidence of the condition is slightly less than 1% of the general population of the U.K. but rises to 5% in the over-65's and to 20% in the over-80's.

The biochemical basis and neuropathology of the disease are better understood than its aetiology. The possibility of a genetic link is being investigated, as are suggestions that aluminium is a causative factor.

Treatments available to date are of, at best, limited value and the progression of the disease is irreversible. Death normally occurs less than a decade after the illness first presents itself (Barker, S. and Branford, D.; Pharm. Journal Jan. 26, 1991, pp 116–118).

4-Aminopyridine (4-AP) has been found to improve the conduction of nerve impulses, thereby, alleviating symptoms in MS patients. 4-AP has been found to slow the potassium ion flow in nerve impulse transmission and, thereby, is effective in restoring conduction in blocked demyelinated nerves. In clinical trials carried out by Davis, F. A. and Stefoski, D. of The Rush Multiple Sclerosis Centre, U.S.A., 4-AP has been administered orally in multiple daily doses over 2–5 days to MS patients with mild to marked improvements being noted and minimal side effects.

3,4-Di-aminopyridine (3,4-DAP) has also been found to improve specific neurological deficits and visual evoked response latencies in MS patients when administered orally in multiple daily doses. Bever, C. T. JR; Leslie, J.; Camenga, D. L.; Panitch, H. S.; and Johnson, K. P., Ann. Neurol. 27(4), pp. 421–427 (Apr. 1990).

4-AP has also been found to improve the mental functions in patients with Alzheimer's disease. This effect is believed to be related to the potassium channel blocking action of 4-AP which in turn enhances calcium influx into the neuron thus prolonging nerve action potential and increasing transmitter release. Wesseling et al., N. Eng. J. of Med. 310(15), pp. 988–989 (Apr. 1984).

In the use of a drag for long-term therapy it is desirable that the drug be formulated so that it is suitable for once- or twice-daily administration to aid patient compliance. Further, in view of the nature of neurological diseases, it can be appreciated that there is a need for an improved dosage form. However, such a formulation must result in a controlled release of drug to the systemic circulation and therapeutically effective blood levels throughout a given treatment period.

Another problem with long-term therapy is the requirement of determining an optimum dose which can be tolerated by the patient. If such a dose is not determined this can lead to a diminution in the effectiveness of the drag being administered.

It is an object of the present invention to provide preparations suitable for the long-term administration of a mono- or di-aminopyridine active agent.

It is a further object of the present invention to provide the use of a mono- or di-aminopyridine active agent in a manner which enables one to achieve a tolerable state for said drug in a subject being treated therewith.

SUMMARY OF THE INVENTION

According to the invention there is provided a pharmaceutical formulation comprising a mono- or di-aminopyridine for administration on a once- or twice-daily basis, said formulation including said mono- or di-aminopyridine active agent in a carrier effective to permit release of said mono- or di-aminopyridine at a rate allowing controlled absorption thereof over, on the average, not less than a 12 hour period and at a rate sufficient to achieve therapeutically effective blood levels over a period of 12–24 hours following administration.

BRIEF DESCRIPTION OF THE DRAWINGS

The accompanying FIGURE is a graph of release of 4-AP (%) versus time (hours) for a patch as prepared in Example 11.

DETAILED DESCRIPTION OF PREFERRED EMBODIMENTS

Figure 1:
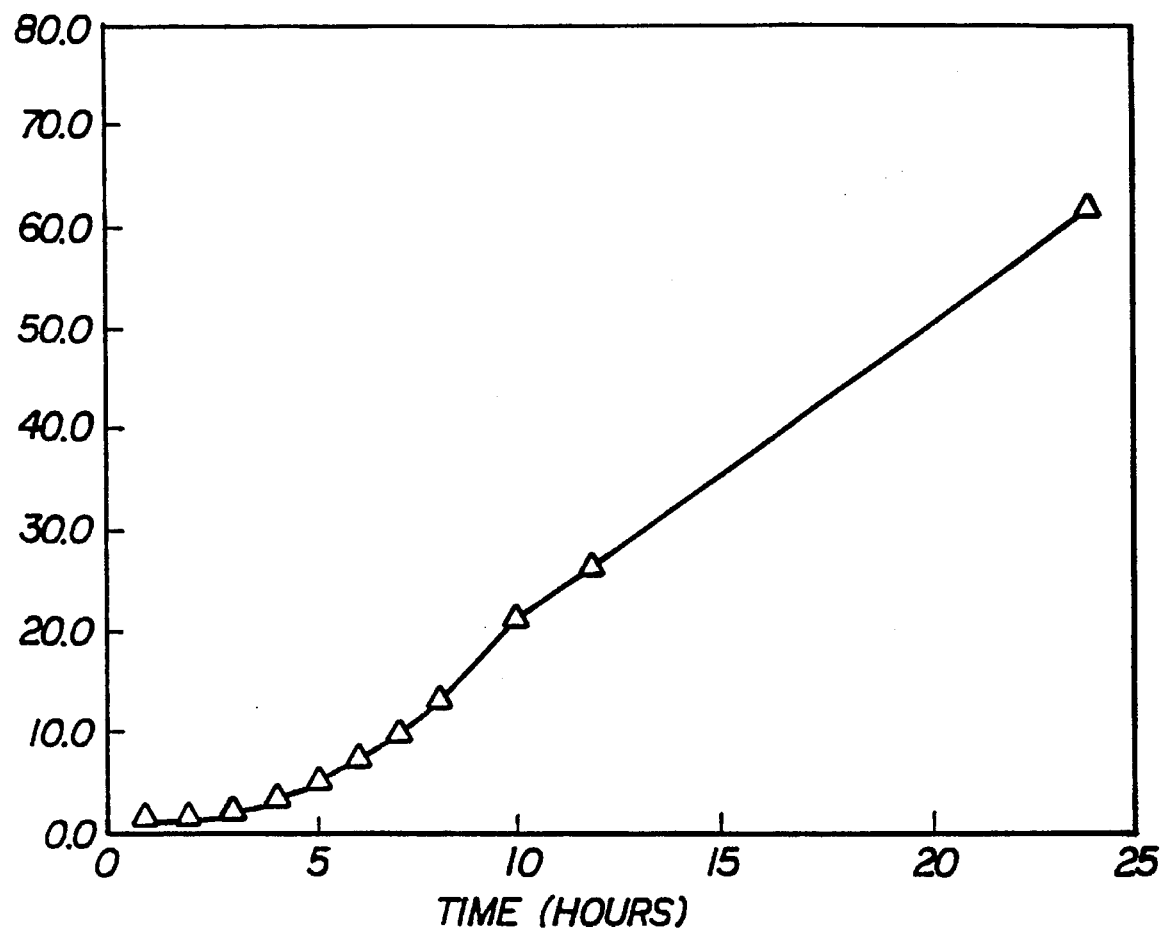

The pharmaceutical formulations according to the invention include pharmaceutical formulations for oral administration and pharmaceutical formulations for administration by the percutaneous route.

According to one aspect of the invention them is provided a pharmaceutical formulation which comprises a pellet for oral administration, said pellet comprising a core of a mono- or di-aminopyridine or a pharmaceutically acceptable salt thereof in association with one or more pharmaceutically acceptable excipient(s), the mono- or di-aminnopyridine component and the pharmaceutically acceptable excipient(s) being present in a ratio of from 10:1 to 1:20, and a multilayer membrane surrounding said core and containing a major proportion of a pharmaceutically acceptable film-forming, water insoluble polymer and optionally a minor proportion of a pharmaceutically acceptable film-forming, water soluble polymer, the number of layers in said membrane and the ratio of said water soluble to water insoluble polymer, when said water soluble polymer is present, being effective to permit release of said mono- or di-aminopyridine from said pellet at a rate allowing controlled absorption thereof over, on the average, not less than a 12 hour period following oral administration, said rate being measured in vitro as a dissolution rate of said pellet, which when measured in a type II dissolution apparatus according to U.S. Pharmacopoeia XXII in water at 50 r.p.m. substantially corresponds to the following:

a) no more than 50% of the total mono- or di-aminopyridine is released after 1 hour of measurement in said apparatus;

b) no more than 75% of the total mono- or di-aminopyridine is released after 4 hours of measurement in said apparatus; and c) 100% of the mono- or di-aminopyridine is released no earlier than after 8 hours of measurement in said apparatus.

Thus the pharmaceutical formulations according to the invention for oral administration can be administered on a once- or twice-daily basis.

Preferred pharmaceutical formulations according to the invention for oral administration are in a multi-particulate form, from which the active agent is released at a rate to maintain therapeutically effective blood levels over a 12 hour period or a 24 hour period, as required.

According to one embodiment, the release of active agent from the pellet is at a rate allowing controlled absorption thereof over a 24 hour period following oral administration, said rate being measured in a type II dissolution apparatus according to U.S. Pharmacopoeia XXII in water at 50 r.p.m. which substantially corresponds to the following dissolution pattern:

a) from 0 to 40% of the total mono- or di-aminopyridine is released after 1 hour of measurement in said apparatus;

b) from 20 to 60% of the total mono- or di-aminopyridine is released after 4 hours of measurement in said apparatus;

c) from 30 to 80% of the total mono- or di-aminopyridine is released after 8 hours of measurement in said apparatus;

d) from 50 to 90% of the total mono- or di-aminopyridine is released after 12 hours of measurement in said apparatus; and e) not less than 75% of the total mono- or di-aminopyridine is released after 24 hours of measurement in said apparatus.

The formulation for once-daily administration can include an amount of a rapid release form of the active agent as hereinafter described, so as to obtain a relatively immediate therapeutic response.

Pharmaceutical formulations according to the invention for once-daily administration can maintain therapeutically effective blood levels substantially over 24 hours with peak plasma levels occurring between 2 and 16 hours, more especially between 4 and 10 hours.

The desired time to peak plasma level is defined as the Tmax of the formulation.

According to a second embodiment, the release of active agent from the pellet is at a rate allowing controlled absorption thereof over a 12 hour period following oral administration, said rate being measured in a type II dissolution apparatus according to U.S. Pharmacopoeia XXII in water at 50 r.p.m. which substantially corresponds to the following dissolution pattern:

a) from 0 to 40% of the total mono- or di-aminopyridine is released after 1 hour of measurement in said apparatus;

b) from 20 to 60% of the total mono- or di-aminopyridine is released after 4 hours of measurement in said apparatus;

c) from 30 to 80% of the total mono- or di-aminopyridine is released after 8 hours of measurement in said apparatus; and d) not less than 75% of the total is released after 12 hours of measurement in said apparatus.

The formulation for twice-daily administration can also include an amount of a rapid release form of the active agent as hereinafter described, so as to obtain a relatively immediate therapeutic response.

Pharmaceutical formulations according to the invention for twice-daily administration can maintain therapeutically effective blood levels substantially over 12 hours with peak plasma levels occurring between 1 and 10 hours, more especially between 2 and 8 hours.

The core of the pellet formulations according to the invention preferably comprises:

a) a powder mixture containing a mono- or di-aminopyridine or a pharmaceutically acceptable salt thereof and a pharmaceutically acceptable excipient, and b) a polymeric material containing a major proportion of a pharmaceutically acceptable water soluble polymer and a minor proportion of a pharmaceutically acceptable water insoluble polymer, said core comprising layers of said powder mixture and said polymeric material superimposed one upon the other and said polymeric material being present in an amount effective to ensure that all of said powder mixture is coated into said core.

The term water soluble polymer as used herein includes polymers which are freely permeable to water, whilst the term water insoluble polymer as used herein includes polymers which are slightly permeable to water, as hereinafter indicated.

Preferably the water soluble polymer in the core or membrane is the same or different and is selected from polyvinyl alcohol, polyvinylpyrrolidone, methyl cellulose, hydroxypropyl cellulose, hydroxypropylmethyl cellulose, agar, carrageenan, xanthan or polyethylene glycol or a mixture thereof.

Alternatively, the water soluble polymer in the core or membrane can be replaced by a polymeric material which is freely permeable to mono- or di-aminopyridine and water and comprises a copolymer of acrylic and methacrylic acid esters.

A suitable polymer which is freely permeable to mono- or di-aminopyridine and water is a polymer sold under the Trade Mark EUDRAGIT RL.

Preferably, the water insoluble polymer in the core or membrane is selected from ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, poly(propylene), poly(ethylene oxide), poly(ethylene terephtalate), poly(vinyl isobutyl ether), poly(vinyl acetate), poly(vinyl chloride) or polyurethane or a mixture thereof.

The water insoluble polymer of the core or membrane may also comprise naturally occurring polymers or resins.

Thus other preferred water insoluble polymers are selected from a naturally occurring polymer selected from shellac, chitosan, gum juniper or a mixture thereof.

Alternatively, the water insoluble polymer in the core or membrane can be replaced by a polymeric material which is slightly permeable to mono- or di-aminopyridine and water and comprises a copolymer of acrylic and methacrylic acid esters.

A suitable polymer which is slightly permeable to mono- or di-aminopyridine and water is a polymer sold under the Trade Mark EUDRAGIT RS or a polymer whose permeability is pH dependent and sold under the Trade Mark EUDRAGIT L, EUDRAGIT S or EUDRAGIT E. Especially preferred polymers in this category are EUDRAGIT S.

EUDRAGIT polymers are polymeric lacquer substances based on acrylates and/or methacrylates. The polymeric materials sold under the Trade Mark EUDRAGIT RL and EUDRAGIT RS are acrylic resins comprising copolymers of acrylic and methacrylic acid esters with a low content of quaternary ammonium groups and are described in the "EUDRAGIT" brochure of Messrs. Rohm Pharma GmbH (1984) wherein detailed physical-chemical data of these products is given. The ammonium groups are present as salts and give rise to the permeability of the lacquer films. EUDRAGIT RL and RS are freely permeable (RL) or slightly permeable (RS), respectively, independent of pH.

EUDRAGIT S is an anionic polymer synthesized from methacrylic acid and methacrylic acid methyl ester. It is insoluble in acids and pure water. It becomes soluble in a neutral to weakly alkaline milieu by forming salts with alkalis. The permeability of EUDRAGIT S is pH dependent. Above pH 6.0 the polymer becomes increasingly permeable. EUDRAGIT S is described in the "EUDRAGIT S" brochure of Messrs. Rohm Pharma GmbH (1986) wherein derailed physical-chemical data of the product is given.

The core suitably has a number of layers of the core-forming materials and is built up in a manner known per se.

The active agent, pharmaceutically acceptable excipient(s) and the polymeric material can be built up on an inert core. The inert core is preferably a non-pareil seed of sugar/starch having an average diameter in the range 0.2–1.4 mm, more especially, 0.3–0.8 mm.

The mono- or di-aminopyridine and pharmaceutically acceptable excipient(s) are blended to form a homogeneous powder. The mono- or di-aminopyridine component and pharmaceutically acceptable excipient(s) are preferably present in a ratio of from 4:1 to 1:5, more especially 1:3 to 1:1.

The blend is suitably passed through an appropriate mesh screen using a milling machine. In the case of coating in a conventional coating pan, alternate layers of a coating solution/suspension of the polymeric material and the powder are applied to the central inert core to build up the multi-layer arrangement of the core. In the case of an automatic coating system, the coating solution/suspension of the polymeric material and the powder are applied, simultaneously, in conventional manner.

The coating solution/suspension of the polymeric material comprises one or more polymer(s) dissolved/suspended in a suitable solvent or mixture of solvents. The concentration of the polymeric material in the coating solution/suspension is determined by the viscosity of the final solution/suspension. Preferably, between 5 and 50 parts of the central inert cores are used relative to the homogeneous powder. The addition of a plasticizing agent to the polymeric solution/suspension may be necessary depending on the formulation to improve the elasticity and also the stability of the polymer film and to prevent changes in the polymer permeability over prolonged storage.

Such changes could affect the drug release rate. Suitable plasticizing agents include polyethylene glycol, propylene glycol, glycerol, triacetin, dimethyl phthalate, diethyl phthalate, dibutyl phthalate, dibutyl sebacate, triethyl citrate, tributyl citrate, triethyl acetyl citrate, castor oil and varying percentages of acetylated monoglycerides.

Alternatively, the active agent, pharmaceutically acceptable excipient(s) and polymeric material can be built up on a central active core. The active core is suitably formed by blending the mono- or di-aminopyridine, pharmaceutically acceptable excipient(s) and polymeric material to form a homogeneous powder, shaping a portion of said blend to form a central core and applying the remainder of said blend alternately or simultaneously with a polymer binding solution to form a layered structure on said central core.

The completed active cores preferably have an average diameter in the range 0.4–1.6 mm, more especially, 0.6–1.2 mm.

The active core is formed by blending mono- or di-aminopyridine, pharmaceutically acceptable excipient(s) and polymeric material to form a homogeneous powder. A portion of the blend is shaped to form a central core. A multi-layer arrangement is then built up by a successive layering and binding process wherein the remainder of the blend and a polymer binding solution are applied to the active core in alternate layers in a conventional coating pan. Alternatively, an automatic coating system may be used wherein the remainder of the blend and polymer binding solution is applied to the active core, simultaneously. Conventional automated coating systems include for example a CF granulator or a Glatt fluidized bed. The cores are formed to assure a uniform distribution of mono- or di-aminopyridine and excipient ingredients throughout the cores.

As indicated above, the pellet formulations for oral administration in accordance with the invention can include an mount of a rapid release form of active agent so as to obtain a relatively immediate therapeutic response, together with the prolonged effects hereinabove described.

Thus according to a third embodiment of the invention there is provided a controlled absorption mono- or di-aminopyridine formulation for oral administation, comprising pellets as hereinbefore defined and including a sufficient quantity of a rapid release form of mono- or di-aminopyridine to ensure prompt achievement of therapeutically effective blood levels together with therapeutically effective blood levels over a 12 to 24 hour period following each oral administration.

A preferred such controlled absorption formulation in accordance with the invention has a dissolution rate which when measured in a type II dissolution apparatus according to U.S. Pharmacopoeia XXII in water at 50 r.p.m. substantially corresponds to the following dissolution pattern:

a) from 20 to 60% of the total mono- or di-aminopyridine is released after 2 hours of measurement in said apparatus;

b) from 30 to 70% of the total mono- or di-aminopyridine is released after 4 hours of measurement in said apparatus;

c) from 50 to 90% of the total mono- or di-aminopyridine is released after 8 hours of measurement in said apparatus; and d) not less than 75% of the total mono- or di-aminopyridine is released after 12 hours of measurement in said apparatus.

A preferred controlled absorption formulation in accordance with the invention for once-daily administration has a dissolution rate which when measured in a type II dissolution apparatus according to U.S. Pharmacopoeia XXII in water and at 50 r.p.m. substantially corresponds to the following dissolution pattern:

a) from 10 to 40% of the total mono- or di-aminopyridine is released after 1 hour of measurement in said apparatus;

b) from 25 to 65% of the total mono- or di-aminopyridine is released after 4 hours of measurement in said apparatus;

c) from 40 to 80% of the total mono- or di-aminopyridine is released after 8 hours of measurement in said apparatus;

d) from 50 to 90% of the total mono- or di-aminopyridine is released after 12 hours of measurement in said apparatus; and e) not less than 75% of the total mono- or di-aminopyridine is released after 24 hours of measurement in said apparatus.

A preferred controlled absorption formulation in accordance with the invention for twice-daily administration has a dissolution rate which when measured in a type II dissolution apparatus according to U.S. Pharmacopoeia XXII in water and at 50 r.p.m. substantially corresponds to the following dissolution pattern:

a) from 20 to 50% of the total mono- or di-aminopyridine is released after 1 hour of measurement in said apparatus;

b) from 30 to 70% of the total mono- or di-aminopyridine is released after 4 hours of measurement in said apparatus;

c) from 40 to 80% of the total mono- or di-aminopyridine is released after 8 hours of measurement in said apparatus; and d) not less than 75% of the total mono- or di-aminopyridine is released after 12 hours in said apparatus.

The controlled absorption formulation according to the invention can comprise a blend of pellets as hereinbefore defined, together with up to 60% by weight of said rapid release form of mono- or di-aminopyridine, more especially 10–40% by weight in the case of a once-daily formulation and 20–50% by weight in the case of a twice-daily formulation.

The rapid release form of the active agent can comprise rapid release pellets or granulates.

Preferably, the rapid release pellets comprise a core of mono- or di-aminopyridine active agent or a pharmaceutically acceptable salt thereof in association with one or more pharmaceutically acceptable excipient(s), the mono- or di-aminopyridine component and the pharmaceutically acceptable excipient(s) being present in a ratio of from 10:1 to 1:20 and a multi-layer membrane surrounding said core and containing a major proportion of a pharmaceutically acceptable film-forming, water soluble polymer and optionally a minor proportion of a pharmaceutically acceptable film-forming, water insoluble polymer, the number of layers in said membrane and the ratio of said water soluble to water insoluble polymer being effective to allow relatively immediate release of the active agent from said pellet.

Further, preferably, the pellets have a dissolution rate, which when measured in vitro in a type II dissolution apparatus according to US Pharmacopoeia XXII in water at 50 r.p.m. substantially corresponds to the following dissolution pattern:

(a) not less than 70% of the total mono- or di-aminopyridine is released after 1 hour of measurement in said apparatus; and (b) not less than 85% of the total mono- or di-aminopyridine is released after 2 hours of measurement in said apparatus.

Depending on the function of the pellets, the polymeric material of the core or membrane will consist solely of a water insoluble polymer or a polymer which is slightly permeable to water and aqueous solutions of mono- or di-aminopyridine. However, the polymeric material of the core or membrane may also consist solely of a water soluble polymer or a polymer which is freely permeably to aqueous solutions of mono- or di-aminopyridine in water, especially in the case of the rapid release pellets.

The polymeric material of the core preferably consists solely of a water insoluble polymer or a polymer which is slightly permeable to water and aqueous solutions of mono- or di-aminopyridine. Alternatively, the polymeric material of the core may consist solely of a water soluble polymer or a polymer which is freely permeable to aqueous solutions of mono- or di-aminopyridine and water as indicated above. The polymeric material of the core may include a combination of a water insoluble polymer with a water soluble polymer. The ratio of water soluble/freely permeable to water insoluble/slightly permeable polymer is determined by the particular combination of polymers selected.

The term pharmaceutically acceptable excipient is used herein to define material(s) which is/are homogeneously mixed with the mono- or di-aminopyridine to form the pellet. These materials may also include ingredients known to act as lubricants. Representative excipients include: microcrystalline cellulose (such as that sold under the Trade Mark AVICEL); colloidal silicon dioxide (such as that sold under the Trade Mark AEROSIL); lactose; talc; starch; sorbitol; and cyclodextrin. These may be used singly or in combination with each other. Especially preferred excipients are talc and lactose.

Preferred coating materials include—solutions/suspensions of the polymers cited for use in the application of the powder blend to the central cores in a suitable organic/aqueous carrier medium.

The membrane of the film-forming polymer or mixture of polymers surrounding the core preferably has a proportion of a polymer which is slightly permeable to mono- or di-aminopyridine and water and optionally a proportion of a water permeable polymer, the ratio of water slightly permeable to water permeable polymer being determined by the inherent permeability characteristics of the polymer(s) selected.

As indicated above, the membrane may also be composed of a proportion of a polymer which is water insoluble and a proportion of a polymer which is water soluble, the ratio of water insoluble to water soluble polymer being determined by the inherent permeability characteristics of the respective polymers.

Normally the ratio of water insoluble/slightly permeable polymers to water soluble/permeable polymers lies between 1:5 and 50:1, more especially 1:2 and 20:1. Examples of each of these types of polymer are described above. Especially suitable water soluble/permeable polymers include polyvinylpyrrolidone, polyvinyl alcohol and EUDRAGIT RL, whilst suitable water insoluble/slightly permeable polymers include ethyl cellulose, cellulose acetate, EUDRAGIT RS, EUDRAGIT L, EUDRAGIT E and EUDRAGIT S. Commercially available ready-made polymeric solutions/suspensions may also be used. These ready-made solutions/suspensions may optionally contain plasticizing agents to improve the polymer film as hereinbefore described. Examples of ready-made solutions/suspensions of polymeric material with or without plasticizing agent include EUDRAGIT RL 30D, EUDRAGIT NE 30D, EUDRAGIT E 12.5, EUDRAGIT L 12.5 P, EUDRAGIT E 12.5, EUDRAGIT S 12.5 P, EUDRAGIT RL 12.5, EUDRAGIT RS 300, EUDRAGIT RS 12.5, AQUACOAT (a Trade Mark of FMC Corporation) and SURE-LEASE (a Trade Mark of Colorcon Inc.).

The water insoluble polymer of the membrane may also comprise naturally occurring polymers or resins. Especially suitable water insoluble, naturally occurring polymers include shellac, chitosan, gum juniper or a mixture thereof.

The membrane may be built up by applying a plurality of coats of membrane polymer solution or suspension to the core as hereinafter described. The membrane solution or suspension contains the polymer(s) dissolved or suspended, respectively, in a suitable aqueous or organic solvent or mixture of solvents, optionally in the presence of a lubricant. Suitable lubricants are talc, stearic acid, magnesium stearate and sodium stearate. A particularly preferred lubricant is talc. The membrane, polymer or mixture of polymers may optionally include a plasticizing agent, the function and choice of which has been previously described.

The dissolution rate achieved is proportionally slower as the amount of membrane applied is increased.

The membrane solution or suspension may be applied to the active cores in a conventional coating pan as indicated or, alternatively, using an automated system such as a CF granulator, for example, a FREUND CF granulator, a GLATT fluidised bed processor, an AEROMATIC, a modified ACCELA-COTA or any other suitably automated bead coating equipment (FREUND, GLATT, AEROMATIC and ACCELA-COTA are all Trade Marks).

Preferably 2–75 ml of membrane solution/suspension is applied per application per kilogram of cores. In an automated system the total amount of membrane solution/suspension applied to the cores is the same as that applied in a conventional coating pan, except that the membrane solution/suspension may be applied continuously.

Preferably, when a coating pan is used the membrane is applied at a rate of 5–30 applications/day until all of the applications have been applied. Between days the pellets are dried for a suitable period of time at a controlled temperature.

The type II dissolution apparatus referred to above is a paddle-type apparatus for carrying out method II according to U.S. Pharmacopoeia XXII.

The pellets or granulates may be compressed into tablets using a binder and/or hardening agent commonly employed in tabletting such as microcrystalline cellulose sold under the Trade Mark "AVICEL" or a co-crystallised powder of highly modified dextrins (3% by weight) and sucrose sold under the Trade Mark "DI-PAC" in such a way that the specific dissolution rate of the pellets is maintained.

Pellets or a combination of pellets in accordance with the invention may also be filled into hard or soft gelatine capsules.

The mono- or di-aminopyridine active agent can form quaternary ammonium-type salts. However, given the solubility of mono- or di-aminopyridines, the formation of pharmaceutically acceptable salts would not normally be required.

According to a further aspect of the invention there is provided a preparation for the once-daily, percutaneous administration of a mono- or di-aminopyridine active agent, which formulation comprises said mono- or di-aminopyridine uniformly distributed in a solid, semi-solid or mucilaginous medium which can be placed in intimate contact with the skin, the release of said mono- or di-aminopyridine from said formulation being at a rate sufficient to achieve therapeutically effective blood levels over a period of 12 to 24 hours following topical application of said preparation.

The invention also provides a preparation for the once-daily, percutaneous administration of a mono- or di-aminopyridine active agent, which formulation comprises said mono- or di-aminopyridine uniformly distributed in a solid, semi-solid or mucilaginous medium which can be placed in intimate contact with the skin, the release of said mono- or di-aminopyridine from said formulation being at a rate allowing controlled absorption thereof over a 24 hour period following topical application of said preparation, said rate being measured in vivo and having a Tmax between 2 and 16 hours.

The formulation for percutaneous administration preferably contains 10–100mg of active agent, more especially 25–75mg of active agent.

The term solidifying agent as used herein also embraces thickening, hardening, setting, suspending or like agents.

Suitable materials for use as the solidifying or gel-forming agent in the preparations according to the invention include, for example, plant extracts, vegetable oils, gums, synthetic or natural polysaccharides, polypeptides, alginates, hydrocarbons, synthetic polymers, minerals and silicon compounds and mixtures thereof.

Suitable plant extracts include agar, ispaghula, psyllium, cydonia and ceratonia or a mixture thereof.

A suitable vegetable oil is hydrogenated castor oil.

Examples of suitable gums include guar gum, acacia gum, ghatti gum, karaya gum, tragacanth gum and xanthan gum or a mixture therof. Such gums are especially suited for use in accordance with the invention.

Suitable synthetic and natural polysaccharides include alkylcelluloses, hydroxalkylcelluloses, cellulose ethers, cellulose esters, nitrocelluloses, dextrin, agar, carrageenan, pectin, furcellaran and starch or starch derivatives and mixtures thereof. An example of a preferred starch derivative is sodium starch glycolate. Especially preferred polysaccharides include agar and carrageenan.

Suitable polypeptides include zein, gelatin, collagen or polygeline or a mixture thereof.

Suitable alginates include alginic acid, propylene glycol alginate or sodium alginate or a mixture thereof.

Preferred hydrocarbons include soft paraffin and hard paraffin, especially white petrolatum.

An especially preferred synthetic polymer is a carboxyvinyl polymer sold under the Trade Mark CARBOMER.

Suitable minerals include bentonite, hectorite, aluminum magnesium silicate and magnesium silicate or a mixture thereof.

Suitable compounds based on silicon include colloidal silicon dioxide, silicones, polysiloxanes and silica gels or a mixture thereof.

The term "agar" as used herein is synonymous with "agar-agar".

The formulation for percutaneous administration is preferably formed by adding a given amount of the active agent to a solution of a solidifying or gel-forming agent or a mixture thereof in a suitable solvent or mixture of solvents and mixing or heating the mixture thereby obtained so as to form said solid, semi-solid or mucilaginous medium.

The solvent used is preferably water. However, the solvent used may also suitably be an alcohol such as ethanol or stearyl alcohol, glycerol, propylene glycol, polyethlene glycol or a silicone or a mixture thereof, including a mixture with water.

The formulation for percutaneous administration when in the form of a solid or semi-solid preferably has a surface area in the range 2 to 15 cm$^2$, more especially 5 to 10 cm$^2$.

The thickness of the formulation for percutaneous administration is preferably in the range 0.5 to 3 mm, more especially in the range 1 to 2 mm.

The formulation for percutaneous administration according to the invention may also include one or more auxilary agent(s) selected from an antimicrobial agent, a preservative, an antioxidant, a pH-controlling agent, a plasticizer, a surfactant, a penetration enhancer, a humectant, a local anaesthetic, an anti-irritant agent or a rubefacient or a mixture thereof.

Suitable antimicrobial agents/preservatives include benzalkonium chloride, cetrimide (cetyltrimethylammonium bromide), benzoic acid, benzyl alcohol, Parabens (Trade Mark for the methyl-, ethyl-, propyl- and butyl-esters of para-hydroxybenzoic acid) chlorhexidine, chlorobutanol, phenylmercuric acetate, borate and nitrate, potassium sorbate, sodium benzoate, sorbic acid and thiomersal (mercurithiosalicylate) or a mixure thereof.

Preferred antioxidants, when used in the formulations for percutaneous administration according to the invention, include sodium metabisulphite, sodium sulphite, butylated hydroxyanisole and butylated hydroxytoluene or a mixture thereof.

Preferred pH-controlling agents, when used in the formulations for percutaneous administration according to the invention, include citric acid and sodium citrate.

Preferred plasticizers, when used in the formulations for percutaneous administration according to the invention, include diethylphthalate, dibutylphthalate and tributylcitrate or a mixture thereof.

Suitable surfactants, when used in the formulations for percutaneous administration according to the invention, include sodium lauryl sulphate, diethylene glycol monostearate, propylene glycol monostearate, polyethylene glycols as sold under the Trade Mark MACROGOL, polysorbates and polyvinyl alcohol or a mixture thereof.

Suitable penetration enhancers, when used in the formulations for percutaneous administration according to the invention, include dimethylsulphoxide, N,N-dimethylacetamide, N,N-dimethylformamide, 2-pyrrolidone, N-methyl-2-pyrrolidone and 1-dodecyl azacyclo-heptan-2-one or a mixture thereof.

A particularly preferred humectant, when used in the formulations for percutaneous administration according to the invention, is glycerol. As indicated above glycerol may also be used as a solvent in forming the formulations for percutaneous administration according to the invention and when used as such will confer humectant properties on said formulation.

Suitable local anaesthetics, when used in the formulations for percutaneous administration according to the invention, include lidocaine, benzocaine, lignocaine, methocaine, butylaminobenzoate and procaine or a mixture thereof. A local anaesthetic would mainly be included to suppress the effects of irritation caused at the site of application of a preparation according to the invention. Suitable anti-irritant agents may also be used such as allantoin, corticosteroids, antihistamines and combinations thereof.

Particularly preferred rubifacients, when used in the formulations for percutaneous administration according to the invention, include camphor and menthol or a mixture thereof and other locally acting peripheral vasodilators.

The formulations for percutaneous administration according to the invention are preferably applied to the flexor surface of the forearm, including the wrist, and also the ankle. Such sites of application show the greatest consistency from individual to individual in terms of drug absorption relative to other sites for administration because of the amount of tissue at such sites. Blood vessels are found close to the surface of the skin at such sites, which facilitates the uptake of active agent into the systemic circulation.

On contact of a formulation for percutaneous administration according to the invention with the skin, the active agent starts to migrate rapidly from the formulation to the humid interface at the point of contact and thence through the skin into the bloodstream. The rate and extent of this percutaneous absorption is dependent on several factors including: the amount of active agent in the formulation; and the surface area of the formulation.

As it is the skin itself that forms the rate controlling barrier and not the dosage form comprising the formulation, the effect of active agent loading will only be observed in terms of systemic active agent levels below a threshold loading level. Below this threshold the amount of active agent in the dosage form is the factor which determines the concentration gradient that in turn controls the rate of absorption. Above this threshold increasing drug loading has no effect on absorption as the ability of the skin to absorb the active agent is saturated. However, such drug loading does have the effect of prolonging the time course of drug delivery by providing a larger drug depot. In order to increase the extent of absorption above the threshold it is necessary to increase the area of absorption by increasing the surface area of the dosage form so that a larger area of the skin is in contact with the active agent.

The formulations for percutaneous administration according to the invention can be presented in a number of devices and dosage forms for the percutaneous administration of the active agent. These devices and dosage forms optionally contain an active agent impermeable layer so as to cause undirectional administration of the active agent through the skin from the surface of the formulation in the device or dosage form exposed to the skin. Such devices and dosage forms include, but are not limited to, a device known under the name DERMAFLEX and which is the subject of our EP-B-0 133 562, devices of the type wherein the drug is contained in a drug reservoir which is separated from the skin by a rate-limiting membrane, self adhesive patches, bandages and plasters, creams, gels, jellies, mucilages, ointments and pastes. The term mucilaginous medium as used herein embraces creams, gels, jellies, ointments and pastes.

The formulations for percutaneous administration according to the invention may be adapted for reception in a receptacle of a device which can be held in contact with the skin.

Means for securing transdermal patches to the body include, apart from adhesive means, straps, bracelets and like securing devices.

The present invention is also designed to provide, through percutaneous administration by way of the said devices and dosage forms, a highly cosmetically and aesthetically acceptable method of easily and discretely administering the active agent to a patient.

In certain cases such as: when the patient is applying a formulation for percutaneous administration according to the invention for the first time or when an individual, who has a particularly high requirement for the active agent is replacing the existing dose, an initial 'burst' or priming dose of active agent may be required to achieve rapid effective plasma levels. The priming dose can be supplied by applying a device or dosage form in which an amount of active agent is included in a layer of adhesive which is used to affix said device or dosage form to the skin. A priming dose of active agent may be included in a layer of adhesive material defining the skin contacting surface of the preparation and which layer is freely permeable to the active agent contained in the solid, semi-solid or mucilaginous agar medium of said preparation. Alternatively, the priming dose of active agent may be included in a peripheral layer of adhesive defining pan of the skin-contacting surface of the formulation.

In order to form the formulation for percutaneous administration according to the invention the thickening, hardening, setting, gelling, suspending or solidifying agent or a mixture of such agents is added to the solvent(s) at a concentration that will result in a suitably mucilaginous, semi-solid or solid mass. The mixture is mixed and/or heated, depending on the agent used, so as to produce a uniform medium. The active agent is added in the required amount so as achieve an amount of active agent in the formulation formed which is preferably 10–100 mg, more especially 25–75 mg. Any other inactive ingredients and auxilary agents as hereinbefore specified are then added and the entire mixture is mixed to uniformity. This mixture is used to form the final dosage form which may be any of the following:
(a) a solid or semi-solid disc or patch formed by moulding, cutting, punching or slicing of the mixture.
(b) a cream.
(c) a mucilage.
(d) a gel.
(e) a paste.
(f) a jelly.
(g) an ointment.

The dosage form may be incorporated into any suitable device for attachment to the skin as indicated above.

When the active agent is a mono-aminopyridine, a particularly preferred mono-aminopyridine is 4-aminopyridine. When the active agent is a di-aminopyridine, a particularly preferred di-aminopyridine is 3,4-DAP.

As stated above, it is believed that 4-AP and 3,4-DAP slow or block the potassium ion flow in nerve impulse transmission. The active agent, therefore, may also be any one of the group of compounds classified as potassium channel blockers, including but not limited to phencyclidine, tetraethylammonium bromide, tetraethylammonium chloride, procaine, quinidine, apamin, amantadine and edrophonium chloride.

The invention also provides a method for the treatment of a neurological disease characterised by a slowing of nerve impulse transmission, which comprises administering to a patient a medicament containing a mono- or di-aminopyridine active agent, said medicament being effective to permit release of said active agent in a manner which achieves therapeutically effective blood levels over a 12–24 hour period when administered on a once- or twice-daily basis.

The mono- or di-aminopyridine active agent is particularly suitable for use in the treatment of a neurological disease which is characterised by demyelination of the central nervous system, more especially multiple sclerosis.

The mono- or di-aminopyridine active agent in accordance with the invention is also suitable for the treatment of Alzheimer's disease.

In one embodiment the medicament is administered to a subject at a dose and for a period sufficient to allow said subject to tolerate said dose without showing any adverse effects and thereafter increasing the dose of said active agent at selected intervals of time until a therapeutic dose is achieved.

In this embodiment of the invention at the commencement of treatment the active agent is preferably administered at a dose less than 15 mg/day until a tolerable state is reached. Suitably when said tolerable state is reached, the dose administered is increased by mounts of at least 5–15 mg/day until said therapeutic dose is reached.

The active agent is preferably 4-aminopyridine or 3,4-diaminopyridine.

The medicament is suitably formulated as a pharmaceutical formulation as hereinbefore specified.

In certain circumstances, the attending physician may consider it appropriate to administer the active agent both orally and percutaneously either simultaneously, separately or sequentially to achieve maximum therapeutic blood levels of said active agent.

The invention will be further illustrated by the following Examples.

EXAMPLE 1

4-AP (8.0 Kg), talc (12.0 Kg) and lactose (36.0 Kg) were blended and milled through a mill equipped with a 50 mesh screen so as to obtain a homogeneous powder. The powder was applied to starch/sugar seeds (0.4–5.0 mm) (12.0 Kg) using a Freund CF granulator and a coating solution of 3.5% polyvinylpyrrolidone in isopropanol to form the cores.

A membrane was then applied to the cores by spraying on a solution consisting of:

| | |
|---|---|
| 12.5% EUDRAGIT S in acetone/ isopropanol 40:60 | 100 parts by weight |
| Isopropanol | 100 parts by weight | while at the same time but separately dusting on talc (100 parts by weight) in conventional manner. The ratio of membrane solution to talc applied was 0.62 g of talc per gram of membrane solution. A sufficient amount of membrane solution and talc was applied to 68.0 Kg of cores to achieve the dissolution profile given below.

The finished pellets were dried to evaporate all solvents prior to performing the dissolution profile.

The dissolution rate of the pellets was tested by method II for the U.S. Pharmacopoeia XXII in water at 50 r.p.m. The dissolution rate was as follows:

| Time | % Release |
|---|---|
| 1 | 0.4 |
| 4 | 34.9 |
| 8 | 68.7 |
| 12 | 85.4 |
| 24 | 99.4 |

The coated beads were blended with active (rapid release) beads in a ratio of 15:85 of active:coated beads by content of 4-AP to generate the following in vitro dissolution profile:

| Time | % Release |
|------|-----------|
| 1 | 14.9 |
| 4 | 42.7 |
| 8 | 73.6 |
| 12 | 89.3 |
| 24 | 100.2 |

EXAMPLE 2

4-AP (4.0 Kg), talc (6.0 Kg) and lactose (18.0 Kg) were blended and milled through a mill equipped with a 50 mesh screen so as to obtain a homogeneous powder. This powder blend was layered into spherical cores using a Freund CF granulator and a coating solution of 3.5% polyvinylpyrrolidone in isopropanol.

A membrane was then applied to the cores by spraying on a solution consisting of:

| | |
|---|---|
| 12.5% EUDRAGIT RS in acetone/isopropanol 40:60 | 50 parts by weight |
| 12.5% EUDRAGIT S in acetone/isopropanol 40:60 | 50 parts by weight |
| Isopropanol | 100 parts by weight | while at the same time but separately dusting on talc (100 parts by weight) in conventional manner. The ratio of membrane solution to talc applied was 0.62 g of talc per gram of membrane solution. A sufficient amount of membrane solution and talc was applied to 28.0 Kg of cores to achieve the dissolution profile given below.

The finished pellets were dried to evaporate all solvents prior to performing the dissolution profile.

The dissolution rate of the pellets was tested by method II for the U.S. Pharmacopoeia in water at 50 r.p.m. The dissolution rate was as follows:

| Time | % Release |
|------|-----------|
| 1 | 1.6 |
| 4 | 25.5 |
| 8 | 58.5 |
| 12 | 79.6 |
| 24 | 97.0 |

On blending with 20% of active beads based on total content of 4-AP the following dissolution profile resulted:

| Time | % Release |
|------|-----------|
| 1 | 19.7 |
| 4 | 40.9 |
| 8 | 64.9 |
| 12 | 81.2 |
| 24 | 96.8 |

EXAMPLE 3

The procedure used was the same as that outlined in Example 2 with the exception that the active beads were formed in a Glatt fluidised coating apparatus.

The active pellets were coated on the Glatt apparatus with a mixture of polymers comprising EUDRAGIT RS:EUDRAGIT S in the ratio 1:2 to achieve the following release profile:

| Time | % Release |
|------|-----------|
| 1 | 2.5 |
| 4 | 29.9 |
| 8 | 69.5 |
| 12 | 96.2 |

These pellets were combined with rapid release pellets in a ratio of 30:70 to generate the following release rates:

| Time | % Release |
|------|-----------|
| 1 | 30.9 |
| 4 | 49.7 |
| 8 | 77.6 |
| 12 | 97.4 |

EXAMPLE 4

The active pellets from Example 3 were coated in a Glatt fluidised bed apparatus using a dispersion of EUDRAGIT polymers in water and containing talc and triacetin. The EUDRAGIT polymers consisted of a ratio of 19:1 of EUDRAGIT RS 30D to EUDRAGIT RL 30D by weight of polymer and the total solid content of the polymer dispersion, including the lubricant (talc) and plasticizer (triacetin) was 23.5%. Following coating and drying, the dissolution rate of the beads according to type II USP apparatus was as follows:

| Time | % Release |
|------|-----------|
| 1 | 4.6 |
| 4 | 39.5 |
| 8 | 61.2 |
| 12 | 76.6 |
| 24 | 86.2 |

When blended with active beads in a ratio of 25:75 of active:coated beads by total content of 4-AP the following dissolution profile in the same apparatus was achieved:

| Time | % Release |
|------|-----------|
| 1 | 28.6 |
| 4 | 54.6 |
| 8 | 70.9 |
| 12 | 82.5 |
| 24 | 91.4 |

EXAMPLE 5

Active 4-AP beads/pellets were formulated according to the procedure set out in Example 1. These active pellets were coated according to the procedure set out in Example 2, however, the application of coats was such as to provide a form of 4-AP suitable for twice daily administration. The dissolution profile of the coated beads was as follows:

| Time | % Release |
|------|-----------|
| 1 | 23.6 |
| 4 | 45.2 |
| 8 | 76.4 |
| 12 | 96.2 |

EXAMPLE 6

Pellets obtained in Example 2 were further coated to the following dissolution rate:

| Time | % Release |
| --- | --- |
| 1 | 1.9 |
| 4 | 21.3 |
| 8 | 53.7 |
| 12 | 83.4 |

On blending with active 4-AP beads in a ratio of 30:70 of active:coated by content of 4-AP, the following dissolution profile resulted:

| Time | % Release |
| --- | --- |
| 1 | 31.6 |
| 4 | 44.2 |
| 8 | 66.8 |
| 12 | 89.1 |

EXAMPLE 7

4-AP (12.0 Kg), talc (8.0 Kg) and lactose (24.0 Kg) were blended and milled through a mill equipped with a 50 mesh screen so as to obtain a homogeneous powder. The powder was applied to starch/sugar seeds (0.5–0.6 mm) (16.0 Kg) using a Freund CF granulator and a coating solution of 3.5% polyvinylpyrrolidone in isopropanol to form the cores.

A membrane was then applied to the cores by spraying on a solution consisting of:

| | |
| --- | --- |
| 12.5% EUDRAGIT RS in acetone/ isopropanol 40:60 | 100 parts by weight |
| Isopropanol | 50 parts by weight | while at the same time but separately dusting on talc (50 parts by weight) in conventional manner. The ratio of membrane solution to talc applied was 0.41 g of talc per gram of membrane solution. A sufficient amount of membrane solution and talc was applied to 60.0 Kg of cores to achieve the dissolution profile given below.

The finished pellets were dried to evaporate all solvents prior to performing the dissolution profile.

The dissolution rate of the pellets was tested by method II for the U.S. Pharmacopoeia XXII in water at 50 r.p.m. The dissolution rate was as follows:

| Time | % Release |
| --- | --- |
| 1 | 1.6 |
| 4 | 29.8 |
| 8 | 59.4 |
| 12 | 77.7 |
| 24 | 92.8 |

The coated beads were blended with active (rapid release) beads in a ratio of 20:80 of active:coated beads by content of 4-AP to generate the following in vitro dissolution profile:

| Time | % Release |
| --- | --- |
| 1 | 21.3 |
| 4 | 43.9 |
| 8 | 66.5 |
| 12 | 82.4 |
| 24 | 93.7 |

EXAMPLE 8

3,4-DAP (8.0 Kg), talc (12.0 Kg) and lactose (36.0 Kg) were blended and milled through a mill equipped with a 50 mesh screen so as to obtain a homogeneous powder. This powder blend was layered into spherical cores using a Freund CF granulator and a coating solution of 3.5% polyvinylpyrrolidone in isopropanol.

A membrane was then applied to the cores by spraying on a solution consisting of:

| | |
| --- | --- |
| 12.5% EUDRAGIT RS in acetone/ isopropanol 40:60 | 50 parts by weight |
| 12.5% EUDRAGIT S in acetone/ isopropanol 40:60 | 50 parts by weight |
| Isopropanol | 100 parts by weight | while at the same time but separately dusting on talc (100 parts by weight) in conventional manner. The ratio of membrane solution to talc applied was 0.62 g of talc per gram of membrane solution. A sufficient amount of membrane solution and talc was applied to 56.0 Kg of cores to achieve the dissolution profile given below.

The finished pellets were dried to evaporate all solvents prior to performing the dissolution profile.

The dissolution rate of the pellets was tested by method II for the U.S. Pharmacopoeia XXII in water at 50 r.p.m. The dissolution rate was as follows:

| Time | % Release |
| --- | --- |
| 1 | 3.7 |
| 4 | 29.6 |
| 8 | 51.4 |
| 12 | 72.6 |
| 24 | 98.4 |

On blending with 25% of active beads based on total content of 3,4-DAP the following dissolution profile resulted:

| Time | % Release |
| --- | --- |
| 1 | 28.2 |
| 4 | 44.3 |
| 8 | 64.2 |
| 12 | 77.1 |
| 24 | 99.3 |

EXAMPLE 9

The procedure used was the same as that outlined in Example 2 with the exception that the active beads were formed in a Glatt fluidised coating apparatus.

The active beads were coated on the Glatt apparatus with a mixture of polymers comprising EUDRAGIT RS:EUDRAGIT S in the ratio 1:2 to achieve the following release profile:

| Time | % Release |
| --- | --- |
| 1 | 3.6 |
| 4 | 28.6 |
| 8 | 60.9 |
| 12 | 88.8 |

These pellets were combined with rapid release pellets in a ratio of 30:70 to generate the following release rates:

| Time | % Release |
| --- | --- |
| 1 | 29.7 |
| 4 | 50.1 |
| 8 | 69.3 |
| 12 | 90.4 |

EXAMPLE 10

The active beads from Example 3 were coated in a Glatt fluidised bed apparatus using a dispersion of EUDRAGIT polymers in water and containing talc and triacetin. The EUDRAGIT polymers consisted of a ratio of 9:1 of EUDRAGIT RS 30D to EUDRAGIT RL 30D by weight of polymer and the total solid content of the polymer dispersion, including the lubricant (talc) and plasticizer (triacetin) was 18.5%. Following coating and drying, the dissolution rate of the beads according to type II USP apparatus was as follows:

| Time | % Release |
| --- | --- |
| 1 | 7.6 |
| 4 | 41.4 |
| 8 | 65.2 |
| 12 | 77.4 |
| 24 | 92.6 |

When blended with active beads in a ratio of 15.8 of active:coated beads by total content of 4-AP the following dissolution profile in the same apparatus was achieved:

| Time | % Release |
| --- | --- |
| 1 | 22.5 |
| 4 | 50.7 |
| 8 | 72.6 |
| 12 | 79.3 |
| 24 | 93.7 |

EXAMPLE 11

To 18.3 g of water was added 0.7 g of carrageenan. This mixture was heated to boiling and then allowed to cool gradually. While still in its liquid state 1.0 g of 4-AP was added and the mixture was agitated to ensure uniformity. 1.0 g portions of the gel, equivalent to 50 mg of 4-AP, were weighed into a preformed circular device of internal diameter 3.2 cm giving a surface area of 8 cm$^2$.

EXAMPLE 12

Patches were prepared as per Example 11 except that 0.5 g of gel was weighed into a preformed circular device of internal diameter 2.3 cm giving a surface area of 4 cm$^2$.

EXAMPLE 13

Patches were prepared as per Example 11 except that 1.5 g of gel was weighed into a preformed circular device of internal diameter 3.9 cm giving a surface area of 12 cm$^2$.

EXAMPLE 14

To 100 g of water was added 10 g of powdered gelatin and 10 g of dextrin. The mixture was heated to boiling. While mixing, the following were also added, 0.01 g of benzalkonium chloride, 0.1 g of sodium metabisulphite, 4.8 g of 4-AP. The hot liquid was poured onto preformed circular discs. Each disc weighed 0.65 g with a surface area of 8 cm$^2$ and each containing 25 mg of 4-AP.

EXAMPLE 15

A product was made as per Example 11 with 0.05 g of methylparaben added to the hot water/carrageenan mixture.

EXAMPLE 16

50 g of stearyl alcohol and 50 g of white petrolatom were melted by heating to 75° C. 0.05 g of methylparaben, 0.3 g of propylparaben, 2 g of sodium lauryl sulphate, 24 g of propylene glycol and 8 g of 4-AP were dissolved in 84 g of water. The aqueous solution was heated to 75° C. and added to the melted stearyl alcohol/petrolatum mixture. The entire mixture was allowed to cool with constant stirring and congealed into a uniform cream. 0.5 g portions of the cream, equivalent to 20 mg of 4-AP, were weighed into circular transdermal delivery devices of internal diameter 2.75 cm giving a surface area of 6 cm$^2$.

EXAMPLE 17

A product was made as per Example 11 except that 1.4 g of 4-AP was added to the water/carrageenan mixture and the patch was cut into rectangular patches measuring 3×4 cm, each weighing 0.9 g with a surface area of 12 cm$^2$.

EXAMPLE 18

To 20 g of water was added 0.8 g of agar. This mixture was heated and allowed to cool gradually, while still in its liquid state 1.1 g of 3,4-diaminopyridine was added and the mixture was agitated to ensure uniformity. The liquid mixture was then poured onto several 20 cm×20 cm glass plates equipped with TEFLON (TEFLON is a Trade Mark) dividers approximately 1.31 mm in height. A second similar glass plate was placed over the liquid supported by the TEFLON dividers. The liquid was allowed to cool to room temperature and solidified into a sheet of uniform thickness (approximately 1.31 mm in thickness). The sheet was then cut into discs, each weighing approximately 0.76 g with a surface area of 5.3 cm$^2$ and each containing 50 mg of 3,4-diaminopyridine. The patches were wrapped in aluminium foil to prevent dehydration.

EXAMPLE 19

To 20 g of water was added 0.8 g of agar. This mixture was heated and allowed to cool gradually, while still in its liquid state 1.11 g of 4-AP was added and the liquid agitated to ensure uniformity. The mixture, while still in the liquid state, was poured into a formed coated aluminium die resulting in a disc of gel of 1.31 mm in thickness and surface area of 5.3 cm$^2$ following solidification and edged around the circumference by 1 cm of aluminium foil. The disc so prepared was then sealed by a coated foil circular seal edged by 1 cm of adhesive. On removal of the seal the disc selectively adhered to the adhesive side of the device, and the aluminium die in which the disc was formed was discarded. The device so prepared provides excellent skin contact in use.

EXAMPLE 20

A product was made according to Example 19 except that the 0.8 g of agar was added to a 20 g 15:5 (w/w) mixture of water and glycerol.

EXAMPLE 21

A product was made according to Example 19 except that the 0.8 g of agar was added to a 20 g 90:10 (w/w) water:ethanol mixture.

EXAMPLE 22

A device was prepared as in Example 19 having a 3,4-diaminopyridine concentration of 60 mg/g with a surface area of 7.64 cm$^2$ and thickness of 1.31 mm.

EXAMPLE 23

A device was prepared as in Example 19 with 0.05 g of methylparaben added to the hot water: agar mixture.

EXAMPLE 24

A device was prepared as in Example 19 with a 15:5 (w/w) mixture of water: PEG (polyethylene glycol) 400 in place of water.

EXAMPLE 25

500 g of water was heated to boiling. 25 g of carrageenan was added and the mixture was boiled for approximately 5–10 minutes. The solution was allowed to cool to between 50° and 60° C. 66 g of 4-AP was added and allowed to dissolve. The solution was diluted to 1,000 g with water. The mixture while still in its liquid state was poured (0.9091 g) into a formed coated aluminium die. The resulting solidified disc had a thickness of 1.30 mm, a surface area of 7.0 cm$^2$ and contained 60 mg of 4-AP. The formed disc was sealed by a circle of aluminium coated with an impervious membrane and a coat of gelatin. On removal of the seal, the disc selectively adhered to the gelatin side of the aluminium seal. Adhesive tape is used to secure the disc to the skin.

EXAMPLE 26

Patches were prepared as in Example 25 except that 55 g of 4-AP was added yielding finished patches of 50 mg/disc.

EXAMPLE 27

Patches were prepared as in Example 25 except that 12.5 g of agar was added instead of 25 g of carrageenan.

EXAMPLE 28

Patches were prepared as in Example 27 except that water: ethanol, 90:10, was used in place of water.

IN VITRO STUDY

The rate of transfer of 4-AP across skin from a disc of the type as prepared in Example 11 was determined in a Franz Cell (Franz, T. J., (1975); J. Invest Dermatol. 64,190) using hairless mouse skin at 37° C. and a phosphate buffer at pH 7.4. The 4-AP transported through the skin was assayed by HPLC. The results are shown in the accompanying Figure.

We claim:

1. A pharmaceutical formulation for the once-daily, percutaneous administration of a mono- or di-aminopyridine active agent for improving nerve conduction, which formulation comprises said mono- or di-aminopyridine uniformly distributed in a solid, semi-solid or mucilaginous medium which can be placed in intimate contact with the skin of a patient in need thereof, the release of said mono- or di-aminopyridine from said formulation being at a rate allowing controlled absorption thereof over a 24 hour period following topical application of said preparation, said rate being measured in vivo and having a Tmax between 2 and 16 hours.

2. A pharmaceutical formulation according to claim 1, which contains from 10–100 mg of mono- or di-aminopyridine active agent.

3. A pharmaceutical formulation according to claim 1, which contains from 25–75 mg of mono- or di-aminopyridine active agent.

4. A pharmaceutical formulation according to claim 1, wherein the solid, semi-solid or mucilaginous medium comprises a gum selected from the group consisting of guar gum, acacia gum, ghatti gum, karaya gum, tragacanth gum, xanthan gum and mixtures thereof.

5. A pharmaceutical formulation according to claim 1, wherein the solid, semi-solid or mucilaginous medium comprises a synthetic or natural polysaccharide selected from the group consisting of alkylcelluloses, hydroxyalkylcelluloses, cellulose ethers, cellulose esters, nitrocelluloses, dextrin, agar, carrageenan, pectin, furcellaran and starch and starch derivative and mixtures thereof.

6. A pharmaceutical formulation according to claim 1, wherein the solid, semi-solid or mucilaginous medium comprises a polypeptide selected from the group consisting of zein, gelatin, collagen, polygeline and mixtures thereof.

7. A pharmaceutical formulation according to claim 1, wherein the solid, semi-solid or mucilaginous medium comprises and alginate selected from the group consisting of alginic acid, propylene glycol alginate, sodium alginate and mixtures thereof.

8. A pharmaceutical formulation according to claim 1, which includes one or more auxiliary agent(s) selected from the group consisting of an antimicrobial agent, a preservative, an antioxidant, a pH-controlling agent, a plasticizer, a surfactant, an enhancer, a humectant, a local anaesthetic, an anti-irritant agent, rubefacient and mixtures thereof.

* * * * *